United States Patent
Notohara et al.

(10) Patent No.: US 8,737,562 B2
(45) Date of Patent: May 27, 2014

(54) BODY SECTION RADIOGRAPHIC APPARATUS, AND A NOISE REMOVING METHOD FOR THE BODY SECTION RADIOGRAPHIC APPARATUS

(75) Inventors: Daisuke Notohara, Kyoto (JP); Kazuyoshi Nishino, Kyoto (JP); Mikihiko Kato, Kyoto (JP); Koichi Shibata, Otsu (JP)

(73) Assignee: Shimadzu Corporation, Kyoto (JP)

( * ) Notice: Subject to any disclaimer, the term of this patent is extended or adjusted under 35 U.S.C. 154(b) by 312 days.

(21) Appl. No.: 12/959,453

(22) Filed: Dec. 3, 2010

(65) Prior Publication Data

US 2012/0140877 A1 Jun. 7, 2012

(51) Int. Cl.
*A61B 6/02* (2006.01)

(52) U.S. Cl.
USPC .............................................. 378/42; 378/26

(58) Field of Classification Search
CPC .............. A61B 6/02; A61B 6/06; A61B 6/25; A61B 6/4291; A61B 6/487; A61B 6/5241; A61B 6/547
USPC ....................... 378/21, 22, 25, 26, 27, 155, 42
See application file for complete search history.

(56) References Cited

U.S. PATENT DOCUMENTS

| | | | |
|---|---|---|---|
| 6,181,773 B1 * | 1/2001 | Lee et al. ........................ | 378/155 |
| 2005/0135558 A1 * | 6/2005 | Claus et al. ..................... | 378/42 |
| 2005/0185755 A1 * | 8/2005 | Okamura ........................ | 378/22 |
| 2005/0213701 A1 * | 9/2005 | Sendai ............................. | 378/8 |

FOREIGN PATENT DOCUMENTS

| | | |
|---|---|---|
| JP | 2004236929 A | 8/2004 |
| JP | 2005-305113 A | 11/2005 |
| JP | 2006-136741 A | 6/2006 |
| JP | 2009297292 A * | 12/2009 |

OTHER PUBLICATIONS

Translation for JP 2006-136741 published on Jun. 1, 2006.*
Notification of Reasons for Refusal for the Application No. 2008-155671 from Japan Patent Office mailed Feb. 14, 2012.
Notification of Reasons for Refusal for the Application No. 2008-155671 Japan Patent Office mailed Dec. 4, 2012.

* cited by examiner

*Primary Examiner* — Glen Kao
(74) *Attorney, Agent, or Firm* — Cheng Law Group, PLLC

(57) ABSTRACT

A body section radiographic apparatus for serially acquiring a series of fluoroscopic images while synchronously moving a radiation source and a radiation detecting device, and obtaining a sectional image of a subject from the series of fluoroscopic images. The apparatus includes, besides the radiation source which emits a beam of radiation and the radiation detecting device which is opposed to the radiation source and has a plurality of radiation detecting elements, a synchronous moving device for moving the radiation source and the radiation detecting device synchronously with each other, and a radiation grid disposed to cover a radiation detecting plane of the radiation detecting device for removing scattered radiation. The fluoroscopic images are serially acquired while moving the radiation grid relative to the radiation detecting device to change positions where radiation transmission unevenness of the radiation grid is projected on the radiation detecting device.

18 Claims, 14 Drawing Sheets

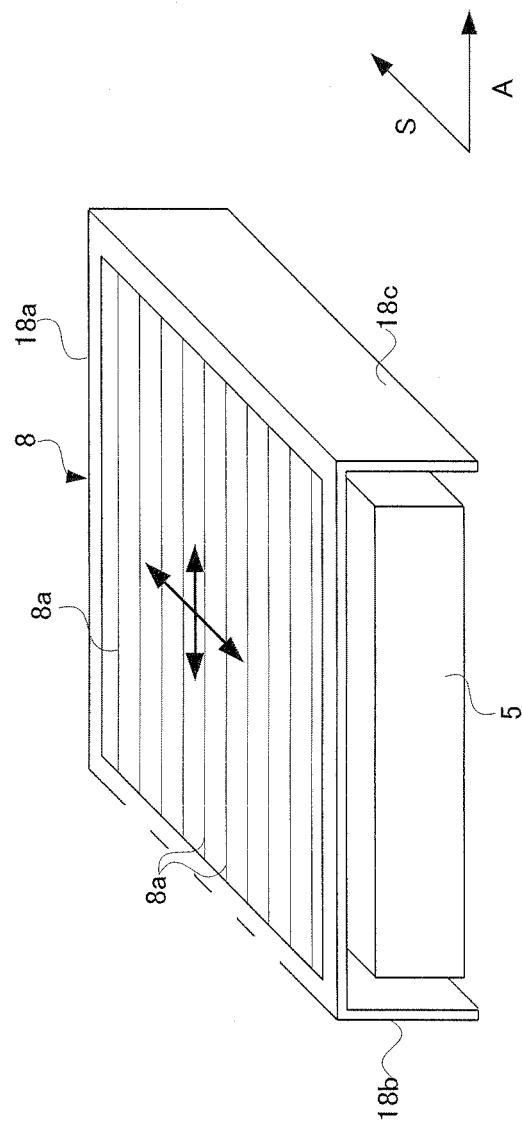

Fig.4
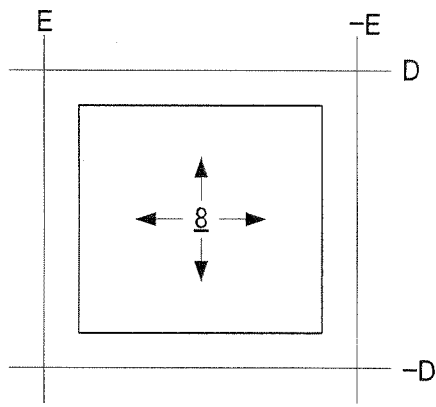
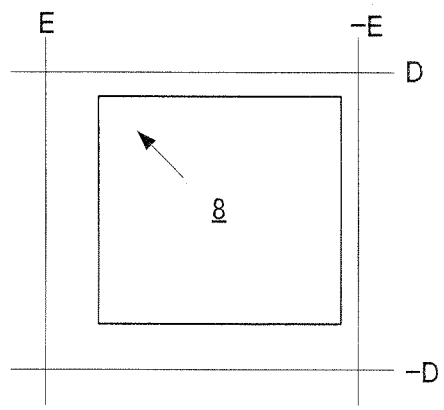
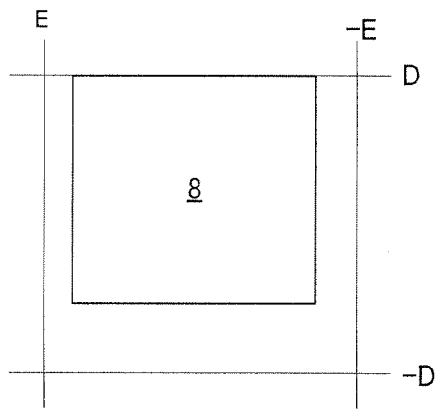
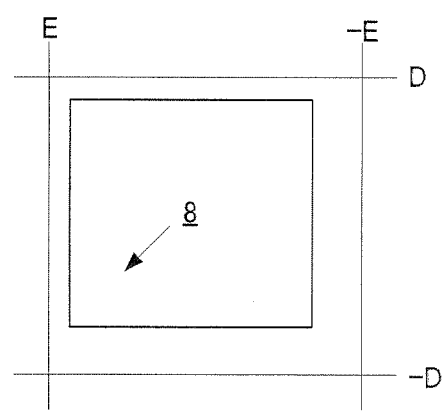
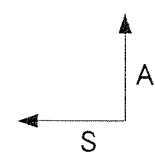

BODY SECTION RADIOGRAPHIC APPARATUS, AND A NOISE REMOVING METHOD FOR THE BODY SECTION RADIOGRAPHIC APPARATUS

BACKGROUND OF THE INVENTION (1) Field of the Invention

This invention relates to a body section radiographic apparatus for repeatedly acquiring fluoroscopic images while synchronously moving a radiation source which emits a beam of radiation to a subject to be imaged and a flat panel detector which acquires fluoroscopic images of the subject, and constructing a sectional images of the subject based on the series of fluoroscopic images obtained. More particularly, the invention relates to a body section radiographic apparatus having a radiation grid disposed between a radiation source and an FPD for transmitting a beam of radiation, and to a noise removing method for use in the body section radiographic apparatus.

(2) Description of the Related Art

Tomographic X-ray apparatus are known as apparatus for acquiring sectional images of subjects using X-rays. Such a tomographic X-ray apparatus serially acquires X-ray fluoroscopic images while synchronously moving an X-ray source and an FPD in opposite directions as opposed to each other across a subject. These X-ray fluoroscopic images are combined to reconstruct, by digital processing, a sectional X-ray image of a desired section of the subject to be displayed on a display device such as a monitor (see Japanese Unexamined Patent Publication No. 2004-236929, for example).

FIG. 13 is a view illustrating a construction of a conventional tomographic X-ray apparatus. A conventional tomographic X-ray apparatus 100 includes an X-ray source 101 for emitting a cone-shaped X-ray beam to a patient M, a sheet like FPD (flat panel detector) 102 for detecting X-rays transmitted through the patient M, a sheet like X-ray grid 103 disposed between the X-ray source 101 and FPD 102 for absorbing scattered X-rays, and a top board 104 for supporting the patient M. The X-ray grid 103 has, arranged therein, a plurality of strip-shaped absorbing foils 103a formed of an X-ray absorbing material. When the X-ray grid 103 is seen as a whole, the plurality of absorbing foils 103a are arranged like slats of a window blind, i.e. parallel to one another and at regular intervals.

The X-ray source 101 and FPD 102 are movable along the direction of the body axis X of the patient M. The sheet like X-ray grid 103 is fixed to the FPD 102. Therefore, the X-ray grid 103 follows movement of the FPD 102 during the serial acquisition of X-ray fluoroscopic images, constantly to prevent scattered X-rays from falling on the FPD 102.

Incidentally, the X-ray grid 103 may have uneven X-ray transmittances at certain parts thereof. In this case, the unevenness of X-ray transmission through the X-ray grid 103 is projected on the FPD 102, to be superimposed on the X-ray fluoroscopic images of the patient M. Then, an X-ray sectional image finally obtained will include granular noise due to the X-ray grid 103. A clear X-ray sectional image cannot be obtained.

In the case of the tomographic X-ray apparatus, the X-ray source 101 and FPD 102 synchronously move in opposite directions as opposed to each other across the patient M. Thus, the position of the X-ray grid 103 relative to the patient M may shift during acquisition of X-ray fluoroscopic images. In that case, the unevenness of transmission through the X-ray grid 103 is appeared as shifting on the X-ray sectional image finally obtained. As a result, the unevenness of X-ray transmission through the X-ray grid 103 cannot be ascertained on the X-ray sectional images.

However, the conventional tomographic X-ray apparatus described above has the following problems. In a particular slice position or section (hereinafter referred to as the grid immobility section MS), there occurs a phenomenon in which the X-ray transmission unevenness of the X-ray grid 103 is not erased from the X-ray sectional image. Moreover, since the X-ray grid 103 is appeared also near the grid immobility section MS, an X-ray sectional image showing a site near the grid immobility section MS has the X-ray transmission unevenness due to the X-ray grid 103 appeared thereon. Thus, a clear X-ray sectional image cannot be obtained.

This grid immobility section MS is determined geometrically from a distance between the X-ray source 101 and FPD 102 (SID: source image distance), a distance between the X-ray source 101 and a reference section MA (SOD: source object distance), and a distance between the X-ray grid 103 and FPD 102 (GID: grid image distance). Generally, values of the above distances cannot be varied, but are constants. Thus, this grid immobility section MS will always appear at a predetermined distance and in a predetermined direction from the reference section MA.

FIG. 14 is a schematic view illustrating how X-ray transmission unevenness due to an X-ray grid in the conventional tomographic X-ray apparatus is projected on an FPD. Point p in the grid immobility section MS is projected on the FPD 102 as moving from point P1 to point P2 and to point P3. When an X-ray sectional image is acquired from this grid immobility section MS, X-ray fluoroscopic images are combined while being shifted so that point P1, point P2 and point P3 may become a fixed point. X-rays having passed through point p in the grid immobility section MS are always transmitted through point gp on the X-ray grid 103 to reach the FPD 102, irrespective of positions of the X-ray source 101 and FPD 102. That is, a shadow of point gp of the X-ray grid 103 is superimposed on point P1, point P2 and point P3 of the FPD 102 corresponding to point p. The same can be said also of point q in the grid immobility section MS. That is, a shadow of point gq of the X-ray grid 103 is superimposed on point Q1, point Q2 and point Q3 of the FPD 102 corresponding to point q.

Incidentally, the X-ray grid 103 has varied X-ray transmittances at certain parts thereof. Supposing, for example, X-ray transmittance at point gp of the X-ray grid 103 is lower than that at point gq, X-rays incident on point P1, point P2 and point P3 will become weaker than X-rays incident on point Q1, point Q2 and point Q3. When an X-ray sectional image is acquired of the grid immobility section MS geometrically determined from the SID, SOD and GID, the X-ray transmission unevenness (particulate noise) of the X-ray grid 103 will be superimposed on the image. For the grid immobility section MS, a method of preventing this particulate noise from being appeared is impossible with the conventional construction.

An X-ray sectional image of the grid immobility section MS acquired with the conventional tomographic X-ray apparatus will have the particulate noise due to the X-ray grid superimposed on the image. Such an image is unsuitable for use in examination. For preventing superimposition of such particulate noise on an X-ray sectional image, it is necessary to acquire X-ray fluoroscopic images serially again after changing the SID, SOD and GID. Then, examination must be conducted twice, which increases exposure to X-rays of the patient. A mechanism is also needed for changing the SID, SOD and GID, making the tomographic X-ray apparatus expensive.

This invention has been made having regard to the state of the art noted above, and its object is to provide a body section radiographic apparatus which is free from radiation transmission unevenness of a radiation grid being appeared on a radiation sectional image irrespective of sections of a subject to be imaged, and a noise removing method for use in the radiographic apparatus.

SUMMARY OF THE INVENTION

The above object is fulfilled, according to this invention, by a body section radiographic apparatus comprising a radiation source for emitting a beam of radiation, a radiation detecting device opposed to the radiation source and having a plurality of radiation detecting elements, a synchronous moving device for moving the radiation source and the radiation detecting device synchronously with each other, and a radiation grid disposed to cover a radiation detecting plane of the radiation detecting device for removing scattered radiation, the apparatus serially acquiring a series of fluoroscopic images while synchronously moving the radiation source and the radiation detecting device, and obtaining a sectional image of a subject from the series of fluoroscopic images, wherein the fluoroscopic images are serially acquired through moving the radiation grid relative to the radiation detecting device to move a position where the sectional image of the subject on a grid immobility section is projected on the radiation detecting device and a position where transmission unevenness of the radiation grid is projected on the radiation detecting device relative to the sectional image having the radiation grid being obtained by fixed support by the radiation detecting device, the grid immobility section being a specific section where the radiation grid is immobile.

With the body section radiographic apparatus according to this invention, the radiation transmission unevenness of the radiation grid never appears on the radiation sectional image irrespective of body sections of the subject. That is, according to the construction of this invention, the fluoroscopic images are serially acquired while the radiation grid and radiation detecting device move relative to each other. Even when a radiation sectional image of a grid immobility section is generated, the radiation transmission unevenness of the radiation grid will be projected on the radiation detecting device while changing positions of the radiation transmission unevenness on the fluoroscopic images. Therefore, the radiation transmission unevenness in the fluoroscopic images will cancel itself only by combining the series of fluoroscopic images. Thus, the radiation sectional image finally obtained is a clear image irrespective of the body sections.

Preferably, the radiation grid is moved relative to the radiation detecting device, in a direction perpendicular to a synchronous moving direction of the radiation source and the radiation detecting device.

The above construction according to the invention can acquire a radiation sectional image from which the radiation transmission unevenness of the radiation grid has been erased with increased reliability. That is, this construction can efficiently move, relative to the radiation detecting device, the radiation grid disposed to cover the radiation detecting device. Since the radiation grid can be moved relative to the radiation detecting device with increased ease, the radiation sectional image provided has granular noise due to the radiation transmission unevenness of the radiation grid removed therefrom reliably.

It is also desirable if the radiation grid is moved relative to the radiation detecting device, along the synchronous moving direction of the radiation source and the radiation detecting device.

The above construction according to the invention can acquire a radiation sectional image from which the radiation transmission unevenness of the radiation grid has been erased with further effect. That is, the position of the radiation grid relative to the radiation detecting device can be changed also in the synchronous moving direction of the radiation source and the radiation detecting device. Thus, the positions where the radiation transmission unevenness of the radiation grid is projected on the radiation detecting device can be changed not only in the direction perpendicular to the synchronous moving direction of the radiation source and the radiation detecting device, but also in the synchronous moving direction of the radiation source and the radiation detecting device. With this construction, the positions where the radiation transmission unevenness of the radiation grid is projected on the radiation detecting device can be changed in the two directions perpendicular to each other. Consequently, the radiation sectional image provided has the radiation transmission unevenness of the radiation grid erased therefrom with increased reliability.

A noise removing method thr a body section radiographic apparatus, according to this invention, comprises moving the radiation source and the radiation detecting device synchronously with each other with a synchronous moving device, the radiation source emitting a beam of radiation, a radiation detecting device being opposed to the radiation source and having a plurality of radiation detecting elements, covering a radiation detecting plane of radiation detecting device with a radiation grind to remove scattered radiation, the noise removing method serially acquiring a series of fluoroscopic images while synchronously moving the radiation source and the radiation detecting device, and obtaining a sectional image of a subject from the series of fluoroscopic images, wherein the fluoroscopic images are serially acquired while moving the radiation grid relative to the radiation detecting device to change positions where radiation transmission unevenness of the radiation grid is projected on the radiation detecting device.

In the above method, it is preferred that the radiation grid is moved relative to the radiation detecting device, in a direction perpendicular to a synchronous moving direction of the radiation source and the radiation detecting device.

And, in the above method, it is preferred that the radiation grid is moved relative to the radiation detecting device, along the synchronous moving direction of the radiation source and the radiation detecting device.

Thus, this invention is directed also to the noise removing method for the body section radiographic apparatus.

This specification discloses also an invention relating to the following body section radiographic apparatus:

(1) In the body section radiographic apparatus, the radiation grid is reciprocated relative to the radiation detecting device, in the direction perpendicular to the synchronous moving direction of the radiation source and the radiation detecting device.

(2) In the body section radiographic apparatus, the radiation grid is reciprocated relative to the radiation detecting device, along the synchronous moving direction of the radiation source and the radiation detecting device.

With the construction described in paragraphs (1) and (2) above, the radiation grid is movable relative to the radiation detecting device in a more complicated way. If the radiation grid were movable in a single direction relative to the radiation detecting device, the transmission unevenness of the radiation grid could be appeared in a section different from the grid immobility section. This is because the transmission unevenness of the radiation grid may not be shifted relative to the radiation image of the subject in that section. According to the above construction, the direction of movement of the radiation grid relative to the radiation detecting device is reversed during a serial acquisition of fluoroscopic images. Under such condition, there remains no section allowing the radiation transmission unevenness of the radiation grid to form an image. Therefore, the position where the transmission unevenness of the radiation grid is appeared in the sectional image of the subject can be changed reliably.

With the body section radiographic apparatus according to this invention, the radiation transmission unevenness of the radiation grid never appears on the fluoroscopic images, also in the grid immobility section. This is because the radiation grid is moved relative to the radiation detecting device. With such construction, since the fluoroscopic images are acquired serially while the radiation grid shifts relative to the fluoroscopic images of the subject in the grid immobility section, the radiation transmission unevenness cancels itself by combining the fluoroscopic images and does not appear in the radiation sectional image. Therefore, granular noise due to the radiation transmission unevenness of the radiation grid does not appear on the radiation sectional image finally obtained.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIG. 3 is a perspective view of the X-ray grid and FPD according to Embodiment 1;

FIG. 4 is a plan view illustrating movement of the X-ray grid relative to the FPD according to Embodiment 1;

DESCRIPTION OF THE PREFERRED EMBODIMENTS

Embodiments of this invention will be described hereinafter with reference to the drawings.

Figure 1:
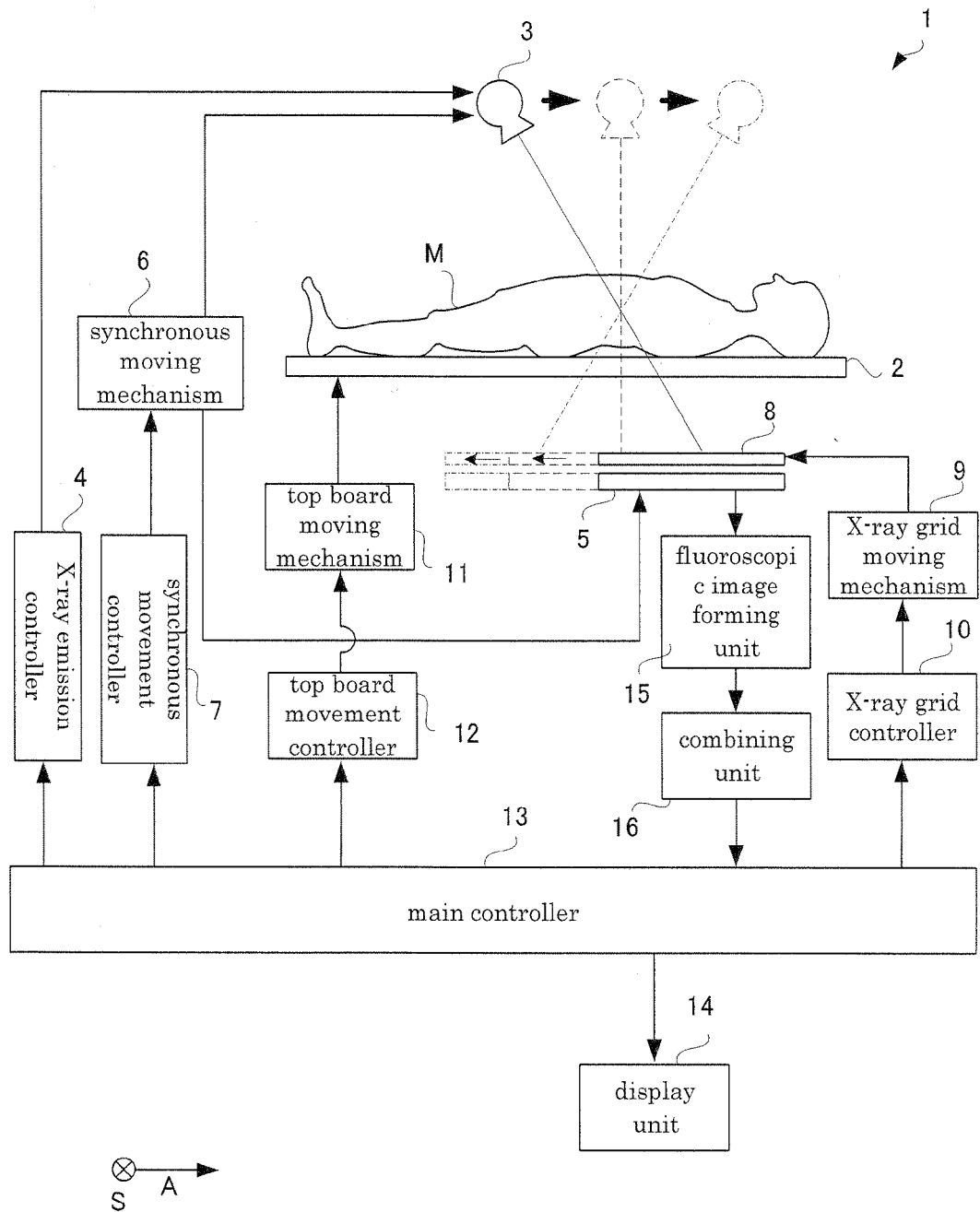
FIG. 1 is a block diagram showing an overall construction of a tomographic X-ray apparatus according to Embodiment 1.

A construction of a tomographic X-ray apparatus according to Embodiment 1 will be described first. FIG. 1 is a block diagram showing an overall construction of a tomographic X-ray apparatus according to Embodiment 1. As shown in FIG. 1, a tomographic X-ray apparatus 1 according to Embodiment 1 includes a top board 2 for supporting a patient M who is a subject of X-ray tomography, an X-ray tube 3 disposed above the top board 2 for emitting a cone-shaped X-ray beam to the patient M, a sheet like flat panel X-ray detector (hereinafter abbreviated as FPD) 5 disposed below the top board 2 for detecting transmitted X-ray images of the patient M, a synchronous moving mechanism 6 for synchronously moving the X-ray tube 3 and FPD 5 in opposite directions as opposed to each other across a site of interest of the patient M and in a state of the center of the cone-shaped X-ray beam and the center of FPD 5 being constantly in agreement, a synchronous movement controller 7 for controlling the synchronous moving mechanism 6, an X-ray grid 8 disposed below the top board 2 to cover an X-ray detecting plane of the FPD 5, an X-ray grid moving mechanism 9 for moving the X-ray grid 8 relative to the FPD 5, and an X-ray grid controller 10 for controlling the X-ray grid moving mechanism 9. X-rays correspond to the radiation in this invention. The X-ray tube, FPD and X-ray grid correspond to the radiation source, radiation detecting device and radiation grid in this invention, respectively.

The X-ray tube 3 is constructed to repeat pulsed irradiation of the patient M with the cone-shaped X-ray beam under control of an X-ray emission controller 4. The X-ray tube 3 has a collimator attached thereto for collimating the X-ray beam into a shape of a pyramid cone. This X-ray tube 3 and FPD 5 constitute a radiographing system for acquiring X-ray fluoroscopic images.

The X-ray apparatus 1 according to Embodiment 1 includes a main controller 13 for performing overall control of the controllers 4, 7 and 10, and a display unit 14 for displaying an X-ray sectional image. The main controller 13 has a CPU and, by executing various programs, realizes the controllers 4, 7 and 10, and a top board movement controller 12, a fluoroscopic image forming unit 15 and a combining unit 16 to be described hereinafter. The synchronous moving mechanims 6 corresponds to the synchronous moving device in this invention.

The top board 2 is vertically movable, and slidable along the direction of the body axis A of the patient M, which is driven by a top board moving mechanism 11. The top board moving mechanism 11 is operable under control of the top board movement controller 12. The top board movement controller 12 is, along with the other controllers 4, 7 and 10, operable under the overall control of the main controller 13.

The synchronous moving mechanims 6 is constructed to move the X-ray tube 3 and FPD 5 synchronously. This synchronous moving mechanims 6, under control of the synchronous movement controller 7, moves the X-ray tube 3 straight along a linear track parallel to the direction of the body axis A of the patient M. Moreover, the cone-shaped X-ray beam emitted from the X-ray tube 3 during examination is always directed toward the site of interest of the patient M. This X-ray emission angle is changed, for example, from an initial angle of −20° to a final angle of 20° by changing an angle of the collimator.

The synchronous moving mechanims 6 moves the FPD 5 disposed below the top board 2, straight along the direction of the body axis A of the patient M, synchronously with straight movement of the X-ray tube 3 noted above. Its moving direction is opposite to the moving direction of the X-ray tube 3. That is, the cone-shaped X-ray beam with the emission source position and the direction of emission changing with movement of the X-ray tube 3 is always received by the entire X-ray detecting plane of the FPD 5. Thus, for one examination, the FPD 5 acquires 74 X-ray fluoroscopic images, for example, while synchronously moving with the X-ray tube 3 in opposite directions. Specifically, the X-ray tube 3 and FPD 5 move, as opposed to each other, through a position shown in dashed lines to a position shown in chain lines. That is, a plurality of X-ray fluoroscopic images are acquired while changing positions of the X-ray tube 3 and FPD 5. Since the cone-shaped X-ray beam is always received by the entire X-ray detecting plane of the FPD 5, the center of the cone-shaped X-ray beam is always in agreement with the center of the FPD 5 during radiography. During radiography, the center of the FPD 5 moves straight, and this movement is opposite to the direction of movement of the X-ray tube 3. That is, the centers of the X-ray tube 3 and FPD 5 move synchronously in opposite directions.

A fluoroscopic image forming unit 15 is provided downstream of the FPD 5 for forming X-ray fluoroscopic images of the patient M based on X-ray detection signals outputted from the FPD 5. Further downstream of this fluoroscopic image forming unit 15 is a combining unit 16 for forming an X-ray sectional image of a desired section of the patient M by combining the plurality of X-ray fluoroscopic images formed in the fluoroscopic image forming unit 15.

Figure 2B:
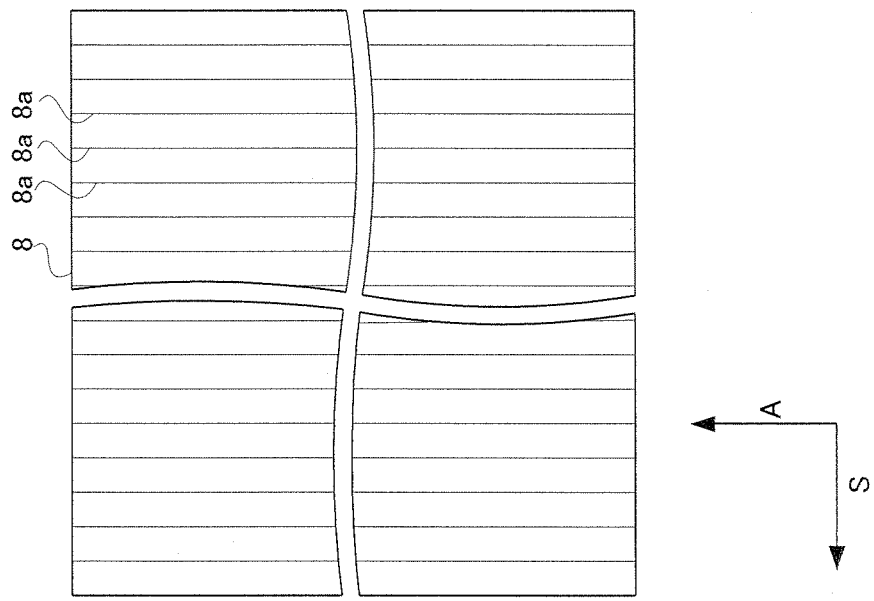
FIG. 2B is a plan view illustrating the X-ray detecting plane of the FPD and the construction of the X-ray grid according to Embodiment 1.
Figure 2A:
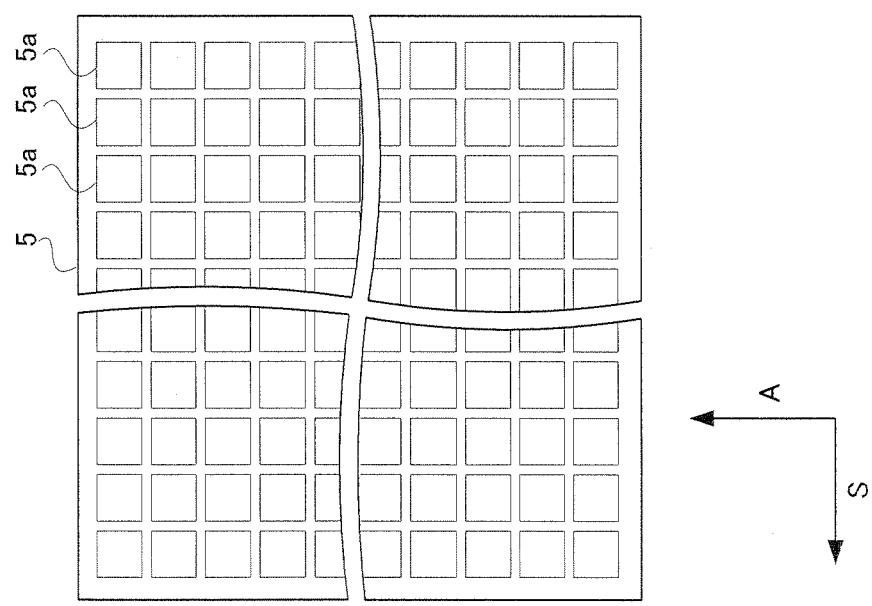
FIG. 2A is a plan view illustrating an X-ray detecting plane of an FPD and a construction of an X-ray grid according to Embodiment 1.

Next, the construction of the FPD 5 will be described. FIG. 2 is a plan view illustrating the X-ray detecting plane of the FPD and the construction of the X-ray grid according to Embodiment 1. As shown in FIG. 2A, the FPD 5 has the X-ray detecting plane for detecting X-rays, which is 30 cm×30 cm. X-ray detecting elements 5a of the semiconductor type are arranged in a matrix form of, for example, 1,024 columns arranged in the direction of the body axis A of the patient M, and 1,024 rows arranged in the transverse direction S of the patient M, for detecting X-rays transmitted through the patient M. That is, the arrangement pitch of X-ray detecting elements 5a is 300 μm both in the direction of rows and in the direction of columns. The FPD 5 has a rectangular shape having four sides along the direction of the body axis A and the transverse direction S of the patient M.

The X-ray grid 8 has a plurality of strip-shaped absorbing foils 8a extending in the direction of the body axis A of the patient M. Each of the absorbing foils 8a absorbs scattered X-rays, and prevents the scattered X-rays from reaching the FPD 5. Of the X-rays proceeding from the X-ray tube 3 toward the FPD 5, scattered X-rays moving in wrong directions such as by being reflected halfway are absorbed by the X-ray grid 8, and do not reach the FPD 5. Thus, the tomographic X-ray apparatus 1 according to Embodiment 1, provided with the X-ray grid 8, can inhibit image blurring and a contrast reduction due to the scattered X-rays. The X-ray beam 17 always falls on the FPD 5 after passing through the X-ray grid 8, irrespective of movement of the X-ray grid 8 relative to the FPD 5.

Next, the construction of X-ray grid 8 will be described. FIG. 3 is a perspective view of the X-ray grid and FPD according to Embodiment 1. As shown in FIG. 3, the X-ray grid 8 provided to cover the FPD 5 includes a main plate 18a and two side plates 18b and 18c arranged at opposite ends of the main plate 18a extending along the transverse direction S of the patient M. The side plates 18b and 18c have a sufficient height to cover the FPD 5. The X-ray grid 8 of such construction is movable along the direction of arrangement and the direction of extension of the absorbing foils 8a by the X-ray grid moving mechanism 9 not shown in FIG. 3. This X-ray grid moving mechanism 9 has a proximal portion thereof fixedly supported by the FPD 5, and a movable portion supporting the X-ray grid 8. The X-ray grid 8 is movable with the FPD 5 along the direction of the body axis A of the patient M by the synchronous moving mechanims 6, and is also movable relative to the FPD 5 along the direction of the body axis A and the transverse direction S of the patient M.

FIG. 4 is a plan view illustrating movement of the X-ray grid relative to the FPD according to Embodiment 1. As shown in the upper left portion of FIG. 4, the X-ray grid 8 is movable relative to the FPD 5 in a range from position −D to position D in the direction of the body axis A of the patient M, and in a range from position −E to position E in the transverse direction S of the patient M. In this way, the X-ray grid 8, driven by the X-ray grid moving mechanism 9, is reciprocable in the transverse direction S and the direction of the body axis A of the patient M relative to the FPD 5. During a serial acquisition of X-ray fluoroscopic images, the X-ray grid 8 makes 2.5 reciprocating motions in the range from position −D to position D, for example, and 2.5 reciprocating motions in the range from position −E to position E, for example. The ranges of the X-ray grid 8 movable in the direction of the body axis A and the transverse direction S of the patient M relative to the FPD 5 is set as 1 cm, for example.

As shown in the upper right portion of FIG. 4, the X-ray grid 8 moves relative to the FPD 5 during a serial acquisition of X-ray fluoroscopic images. With the construction in Embodiment 1, a direction of movement of the X-ray grid 8 relative to the FPD 5 is a sum of two components in the direction of the body axis A of the patient M and the transverse direction S of the patient M which are perpendicular to each other. That is, the X-ray grid 8 is movable in oblique directions relative to the FPD 5. Thus, X-ray fluoroscopic images are acquired serially while changing positions on the FPD 5 which detect the X-ray transmission unevenness of the X-ray grid 8. The X-ray transmission unevenness in Embodiment 1 is a nonuniformity of X-ray intensity occurring when the cone-shaped X-ray beam passes through the X-ray grid 8. The X-ray transmission unevenness occurs planarly due to variations in X-ray transmittance dependent on parts of the X-ray grid 8.

Next, a specific example of movement of the X-ray grid 8 relative to the FPD 5 will be described. Assume that, as shown in the upper right portion of FIG. 4, the X-ray grid 8 is moving relative to the FPD 5 toward position D which is one end of the movable range in the direction of the body axis A of the patient M, and toward position E which is one end of the movable range in the transverse direction S. As shown in the lower left portion of FIG. 4, the X-ray grid 8 reaches position D which is one end of the movable range in the direction of the body axis A of the patient M. Then, as shown in the lower right portion of FIG. 4, the direction of movement in the direction of the body axis A of the patient M is reversed, and the X-ray grid 8 now starts moving toward position −D which is the other end. At this time, the relative movement of the X-ray grid 8 in the transverse direction S of the patient M remains toward position E. At the time of the state shown in the lower left portion of FIG. 4, the movement of the X-ray grid 8 in the transverse direction S of the patient M is not necessarily reversed toward position −E. That is, the movements of the X-ray grid 8 relative to the FPD 5 in the direction of the body axis A and the transverse direction S of the patient M are independent of each other. This arrangement renders the movement of the X-ray grid 8 relative to the FPD 5 further complicated.

Figure 5:
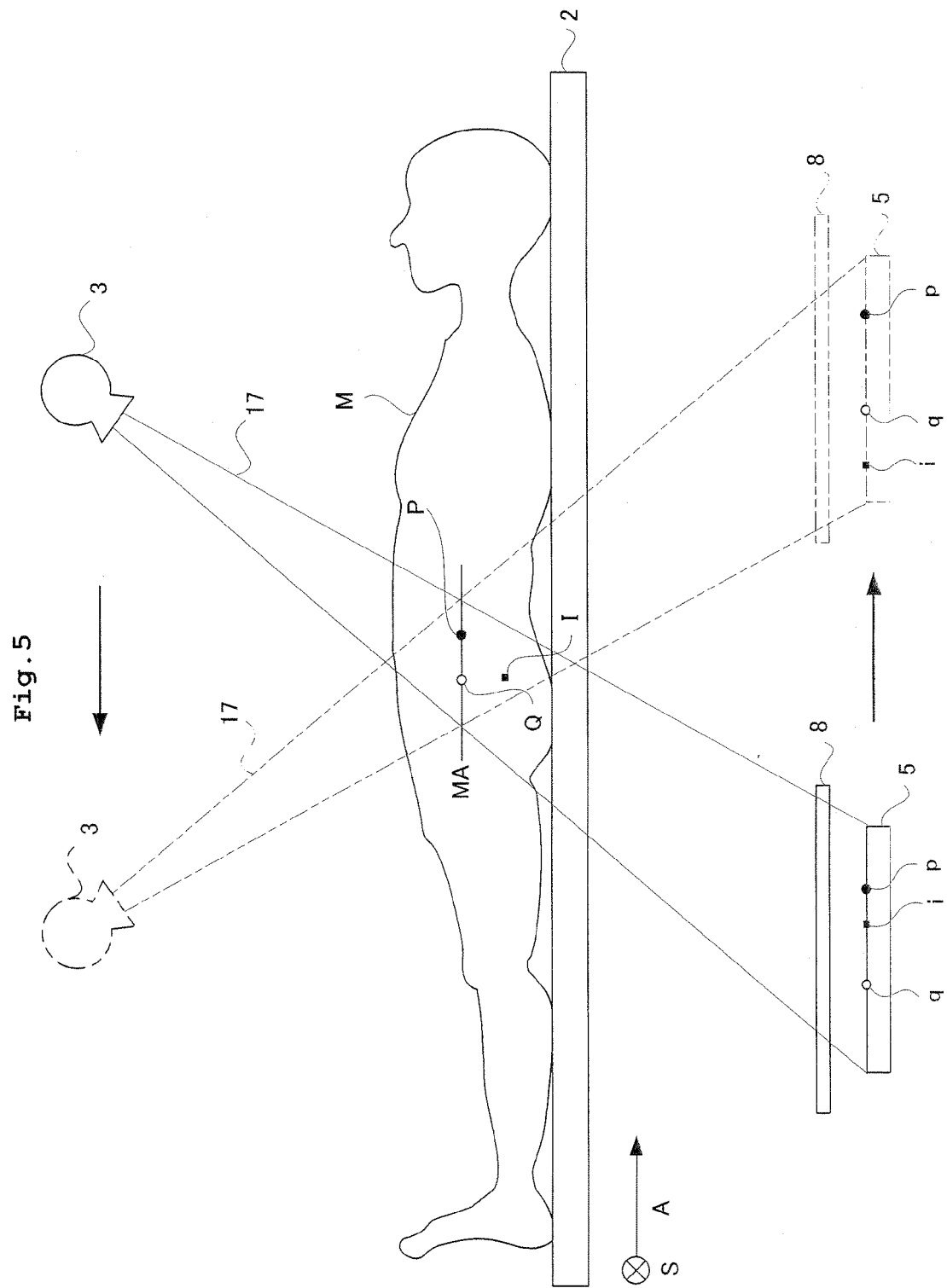
FIG. 5 is a view illustrating a method of acquiring a sectional image with the tomographic X-ray apparatus according to Embodiment 1.

Next, the principle of acquiring a sectional image with the tomographic X-ray apparatus 1 according to Embodiment 1 will be described. FIG. 5 is a view illustrating a method of acquiring a sectional image with the tomographic X-ray apparatus according to Embodiment 1. To describe the principle taking a reference sectional plane MA parallel to the top board 2 as shown in FIG. 5, for example, the fluoroscopic image forming unit 15 continuously forms a plurality of X-ray fluoroscopic images while the FPD 5 is moved synchronously with and in an opposite direction to the X-ray tube 3 according to the direction of emission of the cone-shaped X-ray beam 17, so that points P and Q located in the reference sectional plane MA may always be projected to the respective fixed points p and q on the X-ray detecting plane of the FPD 5. Then, the combining unit 16 combines these X-ray fluoroscopic images, thereby accumulating images located in the reference sectional plane MA (e.g. fixed points p and q), and resulting in an X-ray sectional image. On the other hand, point I not located in the reference sectional plane MA appears in the series of X-ray fluoroscopic images as points i, while changing the projected position on the FPD 5. As distinct from fixed points p and q, such points i become blurred, instead of forming an image, at the stage of combining the X-ray fluoroscopic images in the combining unit 16. An X-ray sectional image showing only the images located in the reference sectional plane MA of the patient M is obtained by combining the X-ray fluoroscopic images in this way. Thus, when a series of X-ray fluoroscopic images are simply combined, an X-ray sectional image of the reference sectional plane MA will be obtained.

Further, a similar X-ray sectional image can be obtained from any selected section parallel to the reference sectional plane MA, by changing settings of the combining unit 16. Although the projected position of point i described above moves on the FPD 5 during radiography, a speed of this movement is determined by a distance between point I before projection and the reference sectional plane MA. By using this to select images having the same moving direction and the same moving speed from the series of acquired X-ray fluoroscopic images, and combining the selected X-ray fluoroscopic images, an X-ray sectional image of a section parallel to the reference sectional plane MA is obtained. Thus, desired X-ray sectional images will be obtained by the combining unit 16 combining the X-ray fluoroscopic images in this way.

Next, a grid immobility section MS will be described. The grid immobility section MS is a specific section where the X-ray grid 8 is immobile relative to an X-ray sectional image, in a tomographic X-ray apparatus having a conventional X-ray grid 8 fixedly supported by the FPD 5. The X-ray transmission unevenness of the X-ray grid 8 appears in X-ray fluoroscopic images serially acquired, while changing its position at a certain speed and in a certain direction. Considering that these X-ray fluoroscopic images detect also X-ray images of the patient M with the moving speed varied according to sections, there exists a section which has a moving speed and direction of its X-ray image in agreement with those of the X-ray transmission unevenness. This means that, when the X-ray fluoroscopic images are combined to obtain an X-ray sectional image of this section, the X-ray transmission unevenness having the same moving speed as the target X-ray image will also be integrated to appear on the X-ray sectional image. This section is the grid immobility section MS in this invention.

Figure 6:
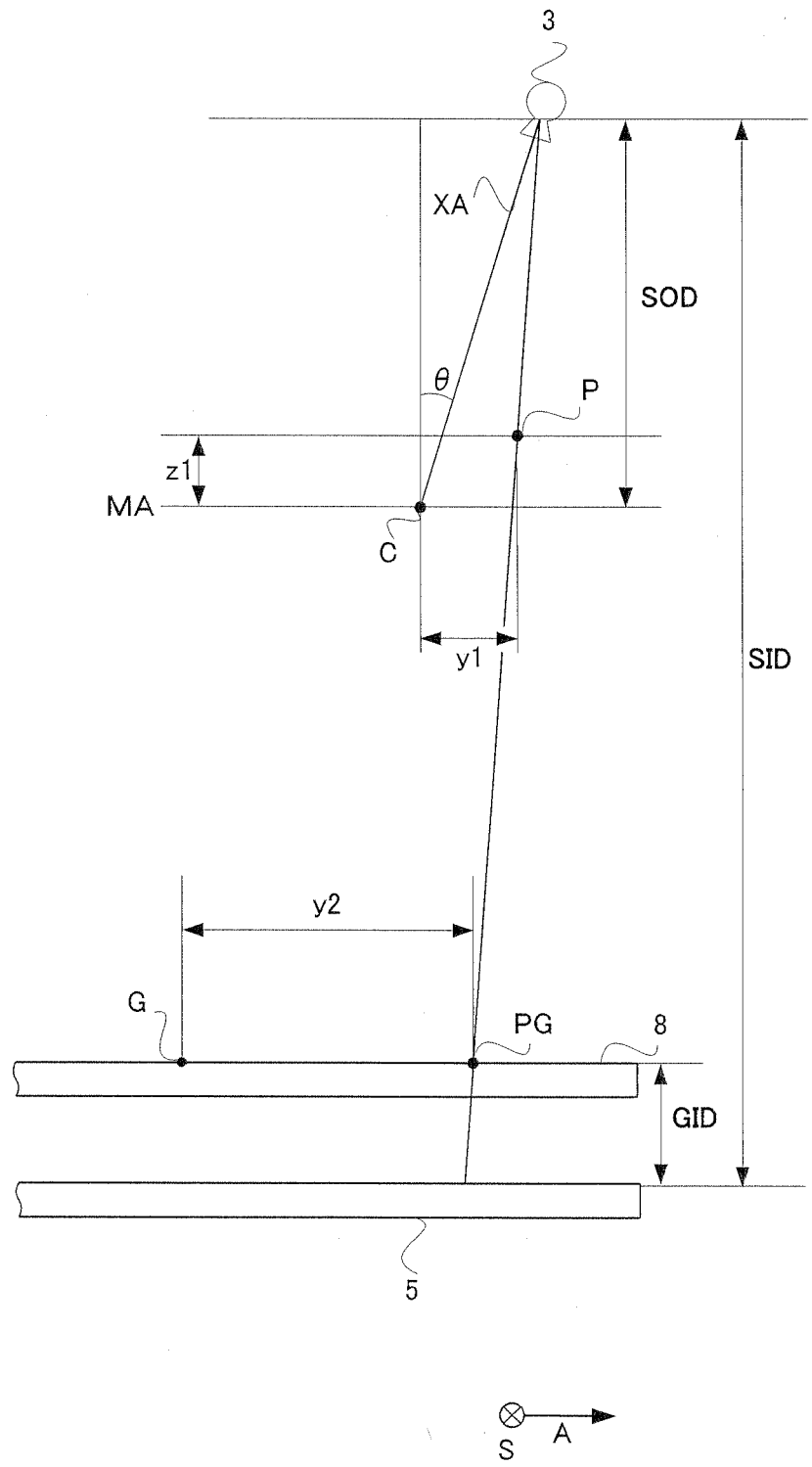
FIG. 6 is a schematic view illustrating a position of appearance of a grid immobility section according to Embodiment 1.

A position of this grid immobility section MS will be described more particularly. FIG. 6 is a schematic view illustrating a position of appearance of the grid immobility section according to Embodiment 1. Now, consider point P shifted z1 in z-direction and y1 in y-direction from the center C of the reference sectional plane MA of the patient M. This center C is a point where the central axis XA of the cone-shaped X-ray beam always passes irrespective of the angle of X-ray emission. The point on the X-ray grid 8 corresponding to point P is set to point PG. Its distance from the center G of the X-ray grid 8 is y2. The X-ray emission angle which is an angle formed between the direction in which the X-ray beam is emitted from the X-ray tube 3 and the vertical direction is set to θ. The center G of the X-ray grid 8 is an intersection of both diagonal lines of the X-ray grid 8.

Generally, y2 changes with θ. However, for a section distanced from the reference sectional plane MA of the patient M by a predetermined value, y2 becomes constant irrespective of angle θ. This section is the grid immobility section MS. The distance between the grid immobility section MS and reference sectional plane MA is determined geometrically from a distance SID between the X-ray tube 3 and FPD 5, a distance SOD between the X-ray tube 3 and reference sectional plane MA, and a distance GID of between the FPD 5 and X-ray grid 8. Generally, y1, y2, z1, θ, SID, SOD and GID are in a relationship expressed by the following equation:

$$y1 = \frac{-z1 \cdot SID\tan\theta - y2(SOD - z1) + GID \cdot SOD\tan\theta}{GID - SID}$$

The value of y2 about fixed point y1 inside the patient M is a function of two variables θ and z1 since SID, SOD and GID are constants, which is expressed as follows by solving the above equation about y2:

$$y2 = \frac{(GID - SID)y1 + (z1 \cdot SID - GID \cdot SOD)\tan\theta}{z1 - SOD}$$

That is, if z1 is equal to GID·SOD/SID, y2 will become a fixed point irrespective of θ. In the tomographic X-ray apparatus 1 according to Embodiment 1, GID, SOD and SID are 24.3 mm, 924 mm and 1,100 mm, respectively, for example, and therefore z1 is calculated to be GID·SOD/SID=20.42 mm. That is, the section distanced by 20.42 mm toward the X-ray tube 3 from the reference sectional plane MA is the grid immobility section MS. If the X-ray grid 8 were not moved relative to the FPD 5, y2 would become a function of one variable y1, and y1 and y2 would be in a one-to-one relationship irrespective of θ. This means that, following the X-ray image of the patient M in the grid immobility section MS, the X-ray grid 8 would be appeared in the 74 X-ray fluoroscopic images. However, if the X-ray grid 8 is moved relative to the FPD 5 as in Embodiment 1, the X-ray grid 8 will not follow the X-ray image of the patient M in the grid immobility section MS. The 74 X-ray fluoroscopic images will be acquired serially while the appearance position of the transmission unevenness of the X-ray grid 8 is shifted relative to the X-ray image of the patient M in the grid immobility section MS.

Figure 7:
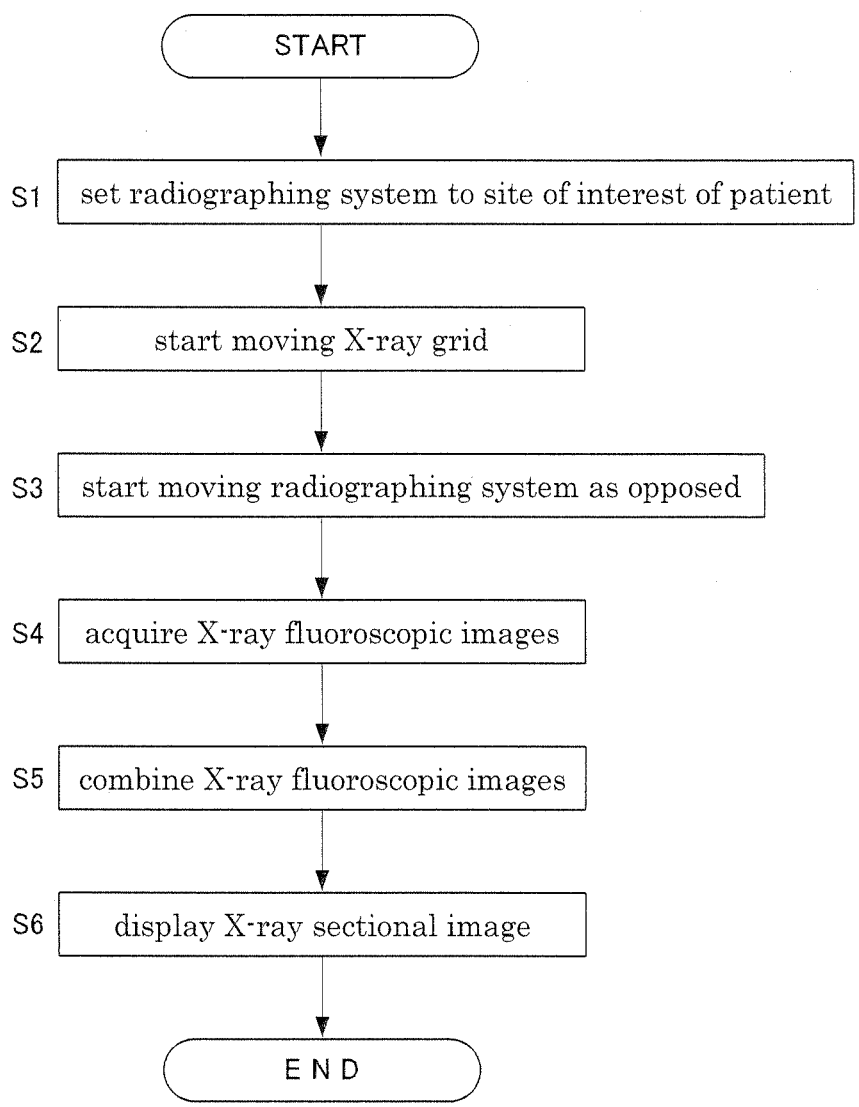
FIG. 7 is a flow chart showing an example of processes of acquiring and displaying a sectional image in the tomographic X-ray apparatus according to Embodiment 1.

Next, processes of acquiring and displaying a sectional image in the tomographic X-ray apparatus 1 according to Embodiment 1 having the above construction will be described with reference to the drawings. FIG. 7 is a flow chart showing an example of processes of acquiring and displaying a sectional image in the tomographic X-ray apparatus according to Embodiment 1. The respective steps constituting the flow chart of FIG. 7 will particularly be described hereinafter.

First, a patient M is laid on the top board 2 and the top board 2 is moved in the direction of the body axis A of the patient M, to set a site of interest of the patient M to a radiographing position (step S1). Next, the X-ray grid 8 is started moving relative to the FPD 5 (step S2). Cone-shaped X-ray beam pulses are emitted toward the patient M on the top board 2 while the X-ray tube 3 is moved synchronously with the FPD 5 (step S3). Subsequently, the fluoroscopic image forming unit 15 acquires 74 X-ray fluoroscopic images required for acquiring an X-ray sectional image (step S4). Further, the combining unit 16 combines the X-ray fluoroscopic images to acquire an X-ray sectional image of a desired section (step S5). Finally, the X-ray sectional image is displayed on the display unit 14 formed of a monitor, for example (step S6), which completes an examination.

In Embodiment 1, as described above, the X-ray transmission unevenness of the X-ray grid 8 never appears on the X-ray fluoroscopic images, also in the grid immobility section MS. This is because the X-ray grid 8 is moved relative to the FPD 5, in the direction of the body axis A and the transverse direction S of the patient M. With such construction, since the X-ray fluoroscopic images are acquired serially while the X-ray grid 8 shifts relative to the X-ray image of the patient M in the grid immobility section MS, the X-ray transmission unevenness is integrated by the combining unit 16 and does not appear in the X-ray sectional image. Therefore, granular noise due to the X-ray transmission unevenness of the X-ray grid 8 is not superimposed on the X-ray sectional image finally obtained.

Figure 8A:
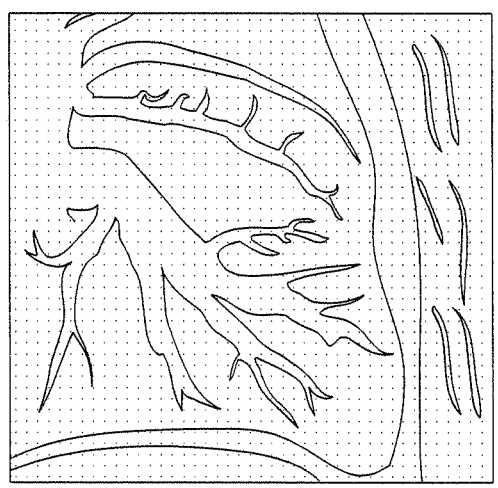
FIG. 8A is a schematic view showing how granular noise due to an X-ray transmission unevenness of the X-ray grid is erased from an X-ray sectional image by the construction of Embodiment 1.
Figure 8B:
FIG. 8B a schematic view showing how the granular noise due to the X-ray transmission unevenness of the X-ray grid is erased from the X-ray sectional image by the construction of Embodiment 1.

Moreover, since the X-ray grid 8 is constructed to reciprocate in the movable range relative to the FPD 5, the movement of the X-ray grid 8 relative to the FPD 5 is further complicated, thereby to change reliably the position where the transmission unevenness of the X-ray grid 8 is appeared in the X-ray sectional image of the patient M. If the X-ray grid 8 were movable in a single direction relative to the FPD 5, the transmission unevenness of the X-ray grid 8 could be appeared in a section different from the grid immobility section MS. This is because the transmission unevenness of the X-ray grid 8 may not be shifted relative to the X-ray image of the patient M in that section. According to the construction of Embodiment 1, the direction of movement of the X-ray grid 8 relative to the FPD 5 is reversed during a serial acquisition of X-ray fluoroscopic images. Under such condition, there remains no section allowing the X-ray transmission unevenness of the X-ray grid 8 to form an image. Therefore, by reciprocating the X-ray grid 8 in the movable range relative to the FPD 5, an X-ray sectional image well suited for examination can be provided with increased reliability. FIG. 8A, 8B is a schematic view showing how granular noise due to the X-ray transmission unevenness of the X-ray grid is erased from an X-ray sectional image by the construction of Embodiment 1. In a conventional construction, the X-ray sectional image in the grid immobility section MS has granular noise superimposed over an entire surface as shown in FIG. 8A. However, according to the construction of Embodiment 1, as shown in FIG. 8B, the X-ray sectional image is free of granular noise, and is well suited for diagnosis.

Embodiment 2

Figure 9:
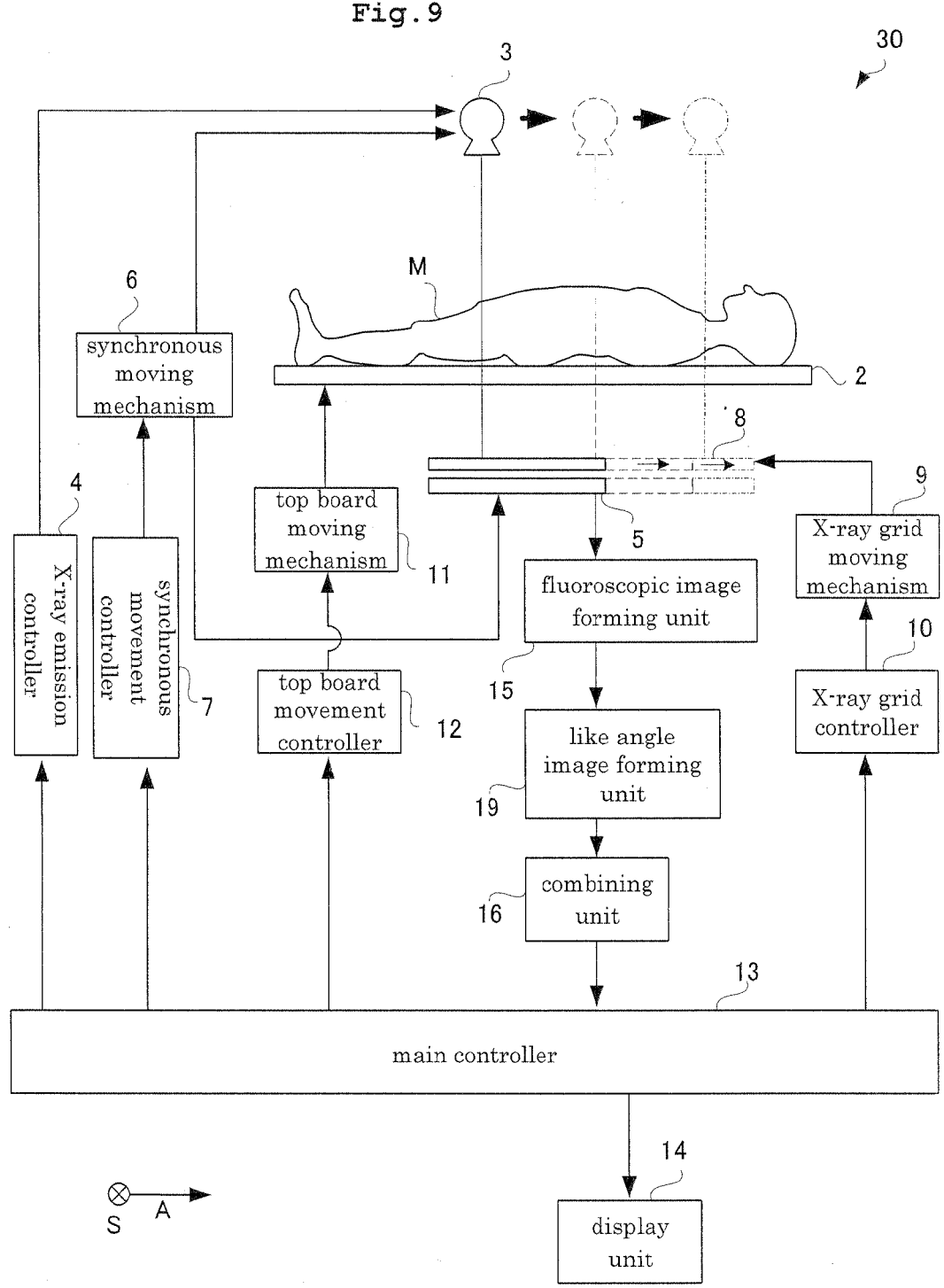
FIG. 9 is a functional block diagram of a tomographic X-ray apparatus according to Embodiment 2.

Next, a tomographic X-ray apparatus 30 according to Embodiment 2 will be described. FIG. 9 is a functional block diagram of a tomographic X-ray apparatus according to Embodiment 2. As shown in FIG. 9, the X-ray apparatus according to Embodiment 2 is similar to the construction described in Embodiment 1. Therefore, description of like components will be omitted as appropriate. The construction of Embodiment 2 is different in the mode of movement of the X-ray tube 3 and FPD 5, and in the mode of image processing of X-ray fluoroscopic images.

The synchronous moving mechanims 6 moves the FPD 5 disposed below the top board 2 straight along the direction of the body axis A of a patient M synchronously with the straight movement of the X-ray tube 3 described above. The moving direction of the FPD 5 is the same as the moving direction of the X-ray tube 3. That is, a cone-shaped X-ray beam with the emission source position and the direction of emission changing with movement of the X-ray tube 3 is always received by the entire X-ray detecting plane of the FPD 5. Thus, for one examination, the FPD 5 acquires 74 X-ray fluoroscopic images, for example, while synchronously moving with the X-ray tube 3 in the same direction. Specifically, the X-ray tube 3 and PD5 move in the same direction through a position shown in dashed lines to a position shown in chain lines.

The cone-shaped X-ray beam emitted from, the X-ray tube 3 during examination is always directed toward a site of interest of the patient M. This X-ray emission angle is constantly at 0° during acquisition of a series of X-ray fluoroscopic images.

The tomographic X-ray apparatus 30 additionally includes a like angle image forming unit 19 interposed between the image forming unit 15 and combining unit 16 for forming like angle images described hereinafter.

Next, the principle of acquiring a sectional image with the tomographic X-ray apparatus 30 according to Embodiment 2 will be described. The 74 X-ray fluoroscopic images acquired serially, after being formed by the image forming unit 15, are outputted to the like angle image forming unit 19 where, for example, 50 like angle images are formed. The 50 like angle images may be combined by the combining unit 16 to acquire a desired X-ray sectional image.

Operation of the like angle image forming unit 19 will be described. The like angle image forming unit 19 first divides each obtained X-ray fluoroscopic image along a direction perpendicular to the synchronous moving direction of the X-ray tube 3 and FPD5 to acquire 50 strip-shaped images, for example. From 3,700(=74×50) strip-shaped images obtained from the series of X-ray fluoroscopic images, the like angle image forming unit 19 selects and joins strip-shaped images having an equal angle of X-ray irradiation, to acquire a like angle image. Since each of the X-ray fluoroscopic images is divided into 50 parts, 50 like angle images are be acquired. Although the X-ray beam according to this invention is cone-shaped, the above process enables accommodation of a reconstructing method in a tomographic X-ray apparatus using a well-known elongate X-ray beam.

Figure 10:
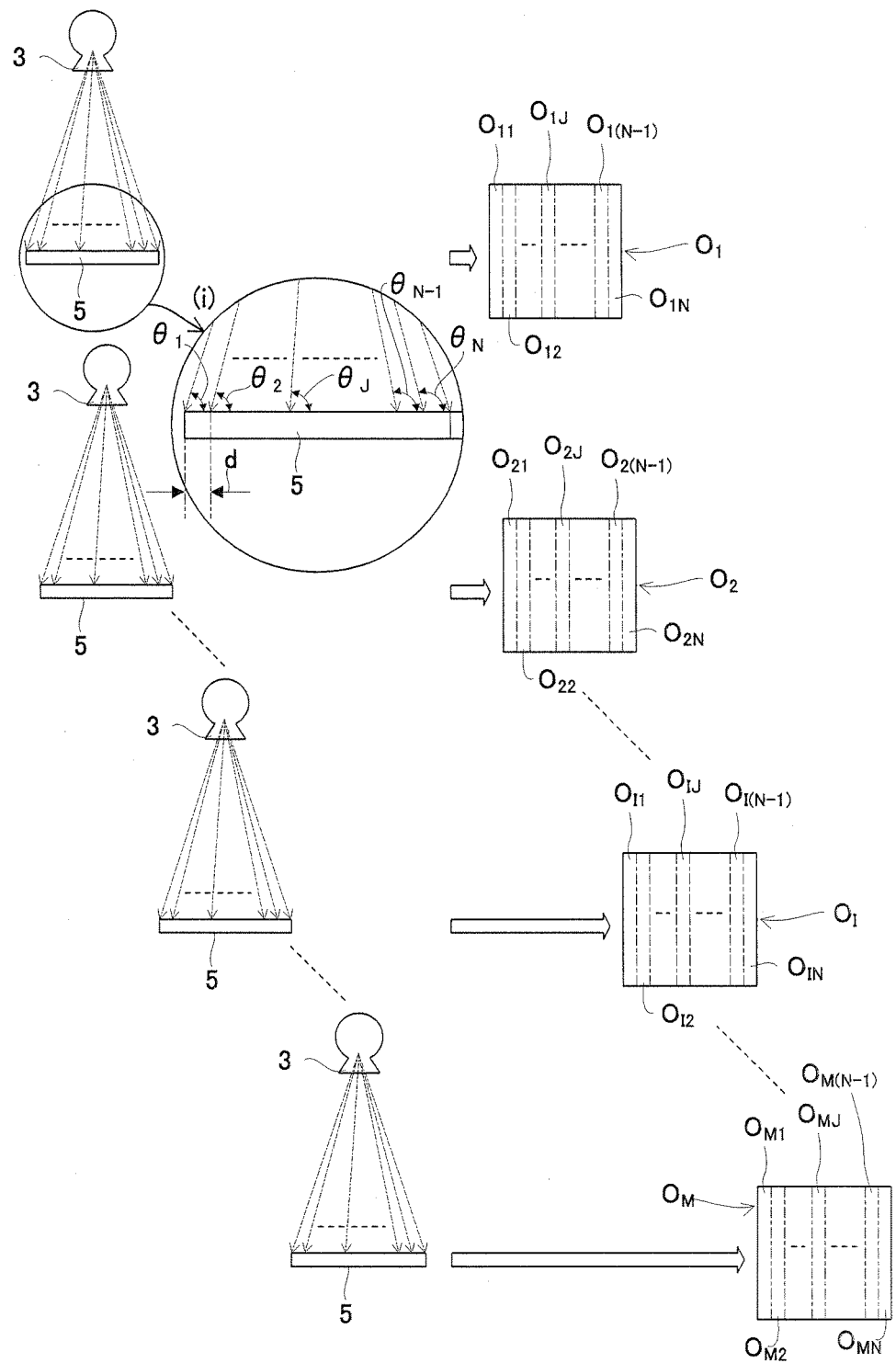
FIG. 10 is a schematic view illustrating image processing by a like angle image forming unit for acquiring an X-ray sectional image according to Embodiment 2.
Figure 11:
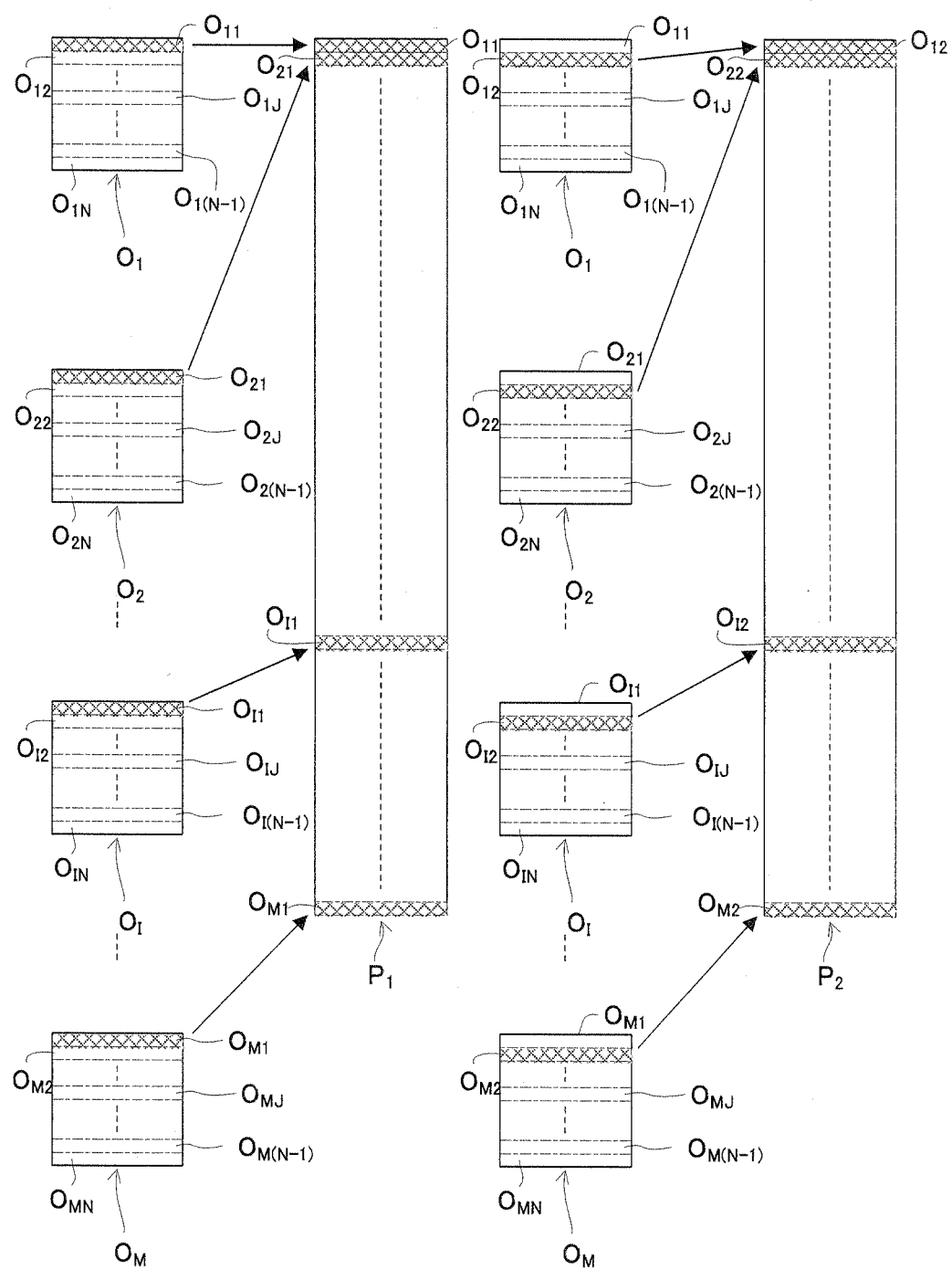
FIG. 11 is a schematic view illustrating image processing by the like angle image forming unit for acquiring an X-ray sectional image according to Embodiment 2.
Figure 12:
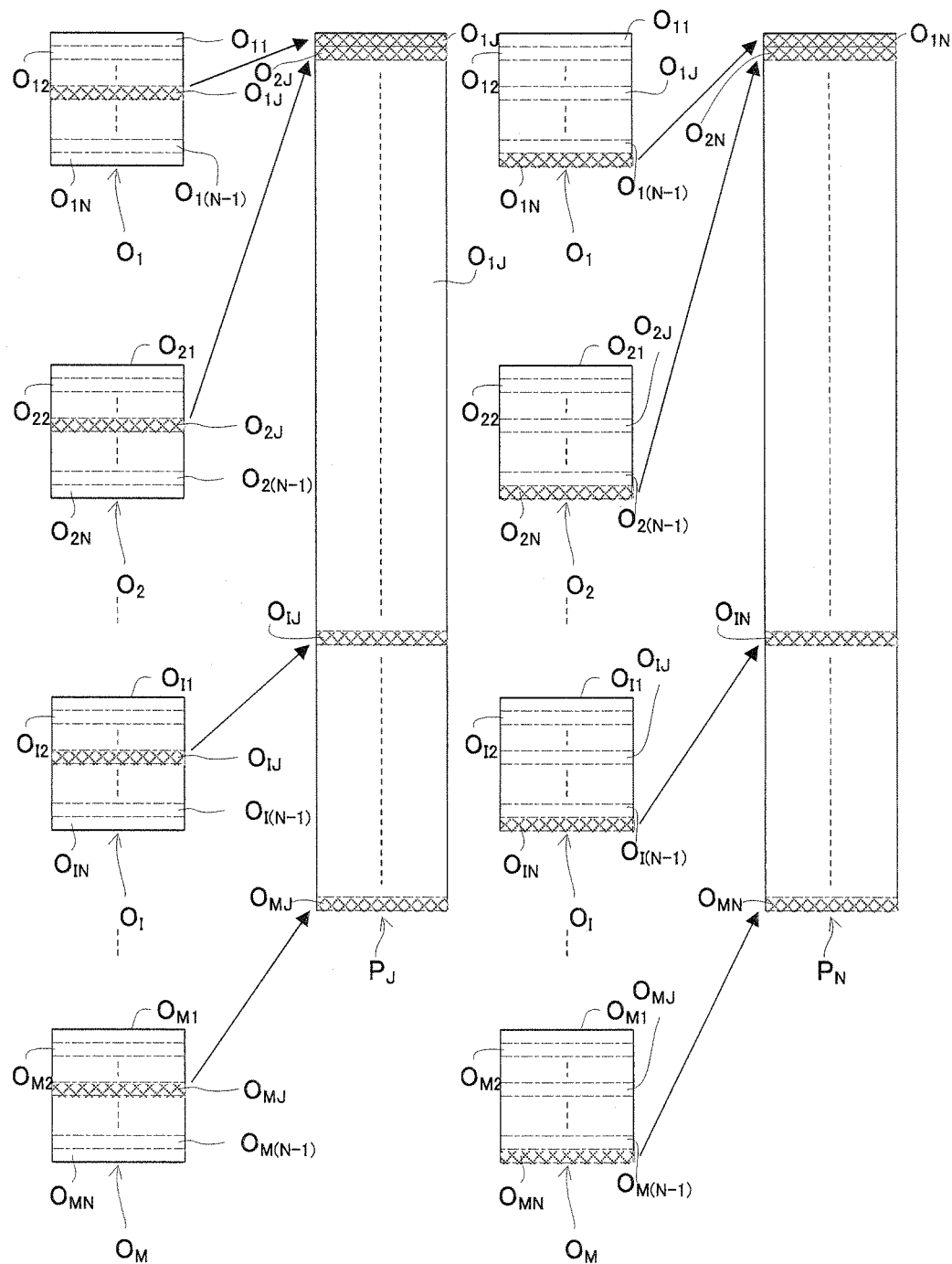
FIG. 12 is a schematic view illustrating the image processing by the like angle image forming unit for acquiring an X-ray sectional image according to Embodiment 2.
Figure 13:
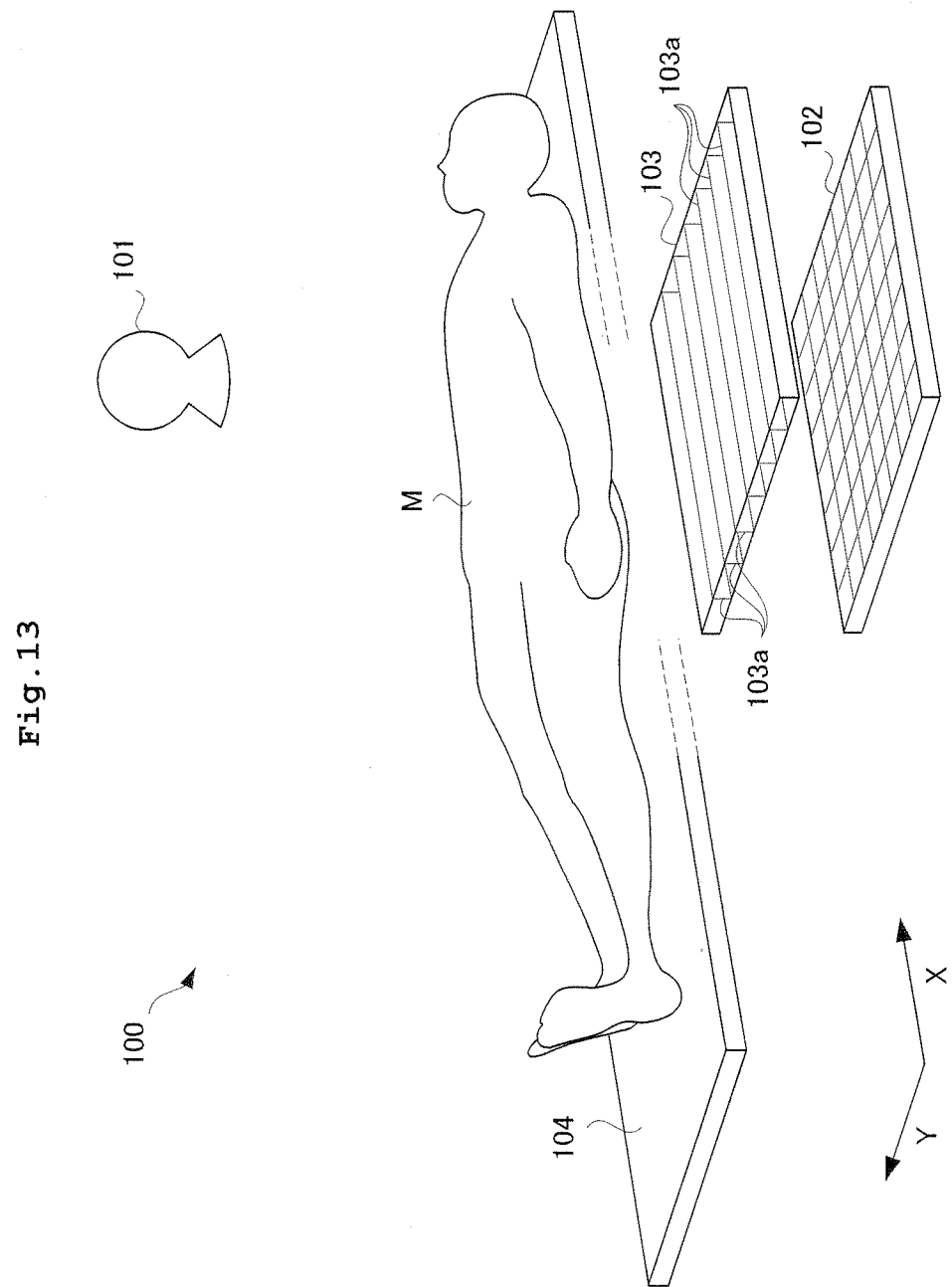
FIG. 13 is a view illustrating a construction of a conventional tomographic X-ray apparatus.
Figure 14:
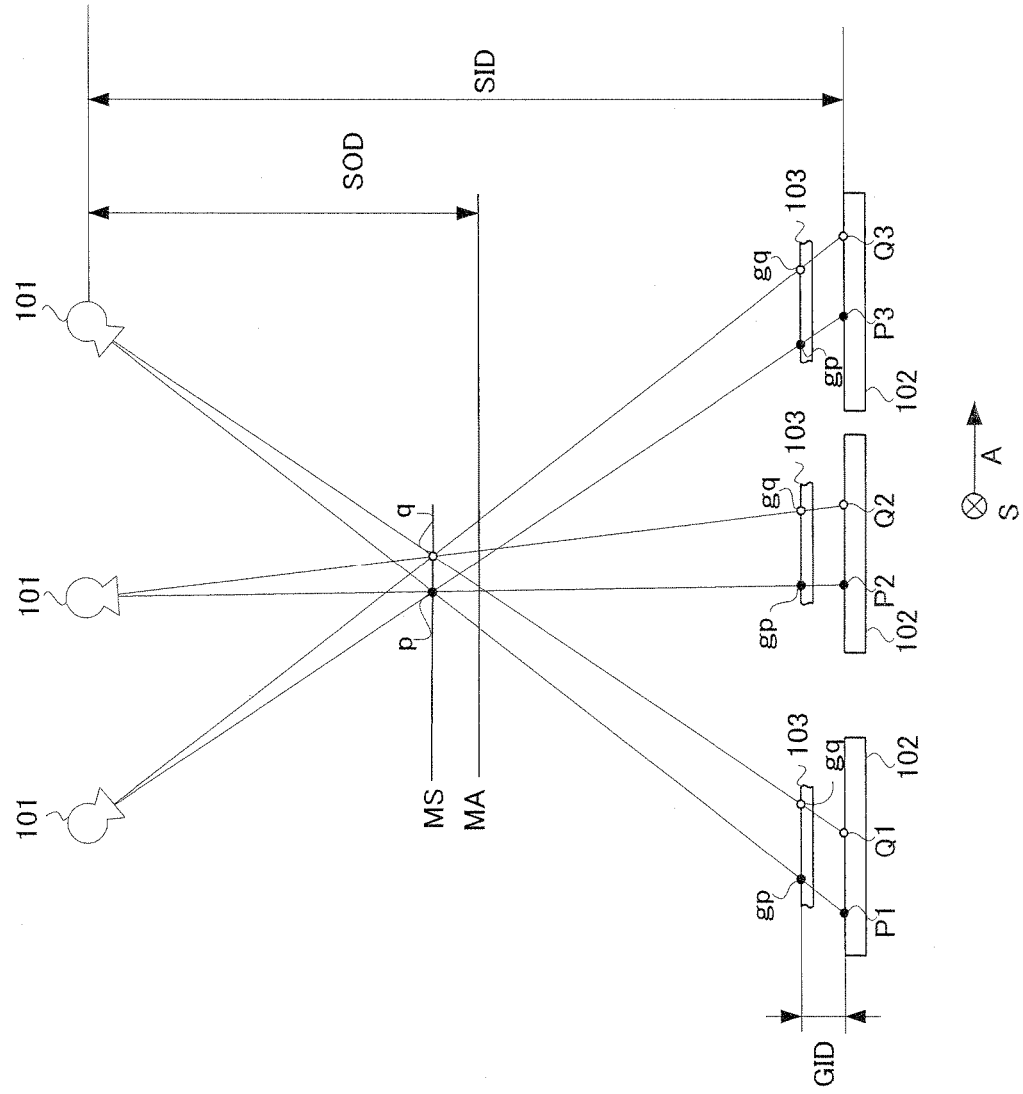
FIG. 14 is a schematic view illustrating how X-ray transmission unevenness due to an X-ray grid in the conventional tomographic X-ray apparatus is projected on an FPD.

The image processing carried out by the like angle image forming unit 19 will be described in greater detail. FIGS. 10 through 12 are schematic views illustrating image processing by the like angle image forming unit for acquiring an X-ray sectional image according to Embodiment 2. Preliminary to the description, it is assumed that, as the X-ray tube 3 moves every pitch d as shown on the left side of FIG. 10, X-ray fluoroscopic images are picked up by the detecting plane of FPD 5, which are referred to as $O_1, O_2, ---, O_I, ---, O_M$ as shown on the right side of FIG. 10 ($1 \leq I \leq M$). While the X-ray tube 3 moves every pitch d, the X-ray tube 3 emits X-rays intermittently. That is, whenever the X-ray tube 3 moves every pitch d, it gives a pulsed irradiation of X-rays. The FPD 5 moves synchronously with the X-ray tube 3.

Specifically, when the X-ray tube 3 emits X-rays first in the position shown at the first stage on the left side of FIG. 10, the X-ray tube 3 emits X-rays next in the position shifted by one pitch d, shown at the second stage on the left side of FIG. 10. The FPD 5 detects the X-rays at the first stage on the left side of FIG. 10, to obtain an X-ray fluoroscopic image $O_1$ (see the first stage on the right side of FIG. 10). The FPD 5 detects the X-rays at the second stage on the left side of FIG. 10, to obtain an X-ray fluoroscopic image $O_2$ (see the second stage on the right side of FIG. 10). Subsequently, the X-ray tube 3, while similarly moving every pitch d, emits X-rays for an (I−1)th time in the position shown at the third stage on the left side of FIG. 10, and the FPD 5 detects the X-rays at the third stage on the left side of FIG. 10, to obtain an X-ray fluoroscopic image $O_I$ (see the third stage on the right side of FIG. 10). Finally, the X-ray tube 3 emits X-rays for an (M−1)th time in the position shown at the fourth stage on the left side of FIG. 10, and the FPD 5 detects the X-rays at the fourth stage on the left side of FIG. 10, to obtain an X-ray fluoroscopic image $O_M$ (see the fourth stage on the right side of FIG. 10). In Embodiment 2, the radiography start position at the first stage on the left side of FIG. 10 is adjacent the feet of the patient M, and the radiography end position at the fourth stage on the left side of FIG. 10 is adjacent the head of the patient M. As the X-ray tube 3 and FPD 5 move from the first stage on the left side of FIG. 10 to the fourth stage on the left side of FIG. 10, movement is made in order along the direction of the body axis A of the patient M.

With the X-ray tube 3 moving every pitch d, each of the X-ray fluoroscopic images $O_1, O_2, ---, O_I, ---, O_M$ can be separated according to pitches d. Specifically, as shown in enlargement in the circle of FIG. 10, projection angles formed between the radiation axis extending from the X-ray tube 3 to the FPD 5 and the body axis of the patient M are set to $\theta_1, \theta_2, ---, \theta_{N\_1}$, and $\theta_N$ for the respective pitches d ($1 \leq J \leq N$). Then, the images separated into the pitches d are in agreement with the strip-shaped images divided into like projection angles $\theta_1, \theta_2, ---, \theta_J, ---, \theta_{N\_1}$ and $\theta_N$, respectively.

The X-ray fluoroscopic image $O_1$ is separated into $O_{11}, O_{12}, ---, O_{1J}, ---, O_{1(N\_1)}$ and $O_{1N}$ according to the pitches d as shown in the first stage on the right side of FIG. 10. The separated strip-shaped image $O_{11}$ is an image derived from the irradiation at projection angle $\theta_1$. The separated strip-shaped image $O_{12}$ is an image derived from the irradiation at projection angle $\theta_2$. Subsequently, the similarly separated strip-shaped image $O_{1J}$ is an image derived from the irradiation at projection angle $\theta_J$. The finally separated strip-shaped image $O_{1N}$ is an image derived from the irradiation at projection angle $\theta_N$.

Similarly, the X-ray fluoroscopic image $O_2$ is separated into $O_{21}, O_{22}, ---, O_{2J}, ---, O_{2(N\_1)}$ and $O_{2N}$ according to the pitches d as shown in the second stage on the right side of FIG. 10. The separated strip-shaped image $O_{21}$ is an image derived from the irradiation at projection angle $\theta_1$. The separated strip-shaped image $O_{22}$ is an image derived from the irradiation at projection angle $\theta_2$. Subsequently, the similarly separated strip-shaped image $O_{2J}$ is an image derived from the irradiation at projection angle $\theta_J$. The finally separated strip-shaped image $O_{2N}$ is an image derived from the irradiation at projection angle $\theta_N$.

For the (I−1)th time, the X-ray fluoroscopic image $O_I$ is separated into $O_{I1}, O_{I2}, ---, O_{IJ}, ---, O_{I(N\_1)}$ and $O_{IN}$ according to the pitches d as shown in the third stage on the right side of FIG. 10. The separated strip-shaped image $O_{I1}$ is an image derived from the irradiation at projection angle $\theta_1$. The separated strip-shaped image $O_{I2}$ is an image derived from the irradiation at projection angle $\theta_2$. Subsequently, the similarly separated strip-shaped image $O_{IJ}$ is an image derived from the irradiation at projection angle $\theta_J$. The finally separated strip-shaped image $O_{IN}$ is an image derived from the irradiation at projection angle $\theta_N$.

Finally, for the (M−1)th time, the X-ray fluoroscopic image $O_M$ is separated into $O_{M1}, O_{M2}, ---, O_{MJ}, ---, O_{M(N\_1)}$ and $O_{MN}$ according to the pitches d as shown in the fourth stage on the right side of FIG. 10. The separated strip-shaped image $O_{M1}$ is an image derived from the irradiation at projection angle $\theta_1$. The separated strip-shaped image $O_{M2}$ is an image derived from the irradiation at projection angle $\theta_2$. Subsequently, the similarly separated strip-shaped image $O_{MJ}$ is an image derived from the irradiation at projection angle $\theta_J$. The finally separated strip-shaped image $O_{MN}$ is an image derived from the irradiation at projection angle $\theta_N$.

The separated images as described above are combined according to the like projection angles $\theta_1, \theta_2, ---, \theta_J, ---, \theta_{N\_1}$ and $\theta_N$, respectively, as shown in FIGS. 11 and 12. As noted above, each of the X-ray fluoroscopic images $O_1, O_2, ---, O_I, ---, O_M$ has images separated according to pitches d (that is, divided into projection angles $\theta_1, \theta_2, ---, \theta_J, ---, \theta_{N\_1}$ and $\theta_N$) as shown in the first column and third column of FIG. 11 and the first column and third column of FIG. 12.

In the case of projection angle $\theta_1$, for example, the strip-shaped image $O_{11}$ in the X-ray fluoroscopic image $O_1$ shown at the first stage in the first column of FIG. 11, the strip-shaped image $O_{21}$ --- in the X-ray fluoroscopic image $O_2$ shown at the second stage in the first column of FIG. 11, the strip-shaped image $O_{I1}$ --- in the X-ray fluoroscopic image $O_I$ shown at the third stage in the first column of FIG. 11 and the strip-shaped image $O_{M1}$ in the X-ray fluoroscopic image $O_M$ shown at the fourth stage in the first column of FIG. 11 are combined to obtain a like angle image $P_1$ for projection angle $\theta_1$ as shown in the second column of FIG. 11.

Similarly, in the case of projection angle $\theta_2$, the strip-shaped image $O_{12}$ in the X-ray fluoroscopic image $O_1$ shown at the first stage in the third column of FIG. 11, the strip-shaped image $O_{22}$ --- in the X-ray fluoroscopic image $O_2$ shown at the second stage in the third column of FIG. 11, the strip-shaped image $O_{I2}$ --- in the X-ray fluoroscopic image $O_I$ shown at the third stage in the third column of FIG. 11 and the strip-shaped image $O_{M2}$ in the X-ray fluoroscopic image $O_M$ shown at the fourth stage in the third column of FIG. 11 are combined to obtain a like angle image $P_2$ for projection angle $\theta_2$ as shown in the fourth column of FIG. 11.

In the case of projection angle $\theta J$, for the (J−1)th time, the strip-shaped image $O_{1J}$ in the X-ray fluoroscopic image $O_1$ shown at the first stage in the first column of FIG. 12, the strip-shaped image $O_{2J}$ --- in the X-ray fluoroscopic image $O_2$ shown at the second stage in the first column of FIG. 12, the strip-shaped image $O_{IJ}$ - - - in the X-ray fluoroscopic image $O_I$ shown at the third stage in the first column of FIG. 12 and the strip-shaped image $O_{MJ}$ in the X-ray fluoroscopic image $O_M$ shown at the fourth stage in the first column of FIG. 12 are combined to obtain a like angle image $P_J$ for projection angle $\theta_J$ as shown in the second column of FIG. 12.

Finally, in the case of projection angle $\theta_N$, for the (N−1)th time, the strip-shaped image $O_{1N}$ in the X-ray fluoroscopic image $O_1$ shown at the first stage in the third column of FIG. 12, the strip-shaped image $O_{2N}$ - - - in the is X-ray fluoroscopic image $O_2$ shown at the second stage in the third column of FIG. 12, the strip-shaped image $O_{IN}$ in the X-ray fluoroscopic image $O_I$ - - - shown at the third stage in the third column of FIG. 12 and the strip-shaped image $O_{MN}$ in the X-ray fluoroscopic image $O_M$ shown at the fourth stage in the third column of FIG. 12 are combined to obtain a like angle image $P_N$ for projection angle $\theta_N$ as shown in the fourth column of FIG. 12.

To summarize the above, the like angle image forming unit 19 combines the images separated according to the like projection angles $\theta_1, \theta_2, ---, \theta_J, ---, \theta_{N-1}$ and $\theta_N$, to obtain like angle images $P_1, P_2, ---, P_J, ---,$ and $P_N$ for projection angles $\theta_1, \theta_2, ---, \theta_J, ---, \theta_{N-1}$ and $\theta_N$, as shown in the second column and fourth column of FIG. 11 and the second column and fourth column of FIG. 12.

The combining unit 16 obtains a sectional image by carrying out a reconstruction process based on the combined like angle images $P_1, P_2, ---, P_J, ---,$ and $P_N$. The reconstruction process may be carried out using the well-known filtered back projection (FBP).

Also in the construction of Embodiment 2, the X-ray transmission unevenness of the X-ray grid 8 appears on the X-ray fluoroscopic images in the grid immobility section MS described in Embodiment 1. Thus, the X-ray grid 8 according to Embodiment 2 is constructed movable relative to the FPD 5 to prevent this X-ray transmission unevenness from appearing on the X-ray fluoroscopic images.

A method of moving the X-ray grid 8 according to Embodiment 2 will be described. FIG. 4 is a plan view illustrating movement of the X-ray grid relative to the FPD in the tomographic X-ray apparatus according to Embodiment 1, which is applicable also to the tomographic X-ray apparatus 30 according to Embodiment 2. That is, as shown in the upper left portion of FIG. 4, the X-ray grid 8 is movable relative to the FPD 5 in a range from position −D to position D in the direction of the body axis A of the patient M, and in a range from position −E to position E in the transverse direction S of the patient M. In this way, the X-ray grid 8, driven by the X-ray grid moving mechanism 9, is reciprocable in the transverse direction S and the direction of the body axis A of the patient M relative to the FPD 5. During a serial acquisition of X-ray fluoroscopic images, the X-ray grid 8 makes 2.5 reciprocating motions in the range from position −D to position D, for example, and 2.5 reciprocating motions in the range from position −E to position E, for example. The ranges of the X-ray grid 8 movable in the direction of the body axis A and the transverse direction S of the patient M relative to the FPD 5 is set as 1 cm, for example.

As shown in the upper right portion of FIG. 4, the X-ray grid 8 moves relative to the FPD 5 during a serial acquisition of X-ray fluoroscopic images. With the construction in Embodiment 2, a direction of movement of the X-ray grid 8 relative to the FPD 5 is a sum of two components in the direction of the body axis A of the patient M and the transverse direction S of the patient M which are perpendicular to each other. That is, the X-ray grid 8 is movable in oblique directions relative to the FPD 5. Thus, X-ray fluoroscopic images are acquired serially while changing positions on the FPD 5 which detect the X-ray transmission unevenness of the X-ray grid 8. The X-ray transmission unevenness in Embodiment 1 is a nonuniformity of X-ray intensity occurring when the cone-shaped X-ray beam passes through the X-ray grid 8. The X-ray transmission unevenness occurs planarly due to variations in X-ray transmittance dependent on parts of the X-ray grid 8.

Next, a specific example of movement of the X-ray grid 8 relative to the FPD 5 will be described. Assume that, as shown in the upper right portion of FIG. 4, the X-ray grid 8 is moving relative to the FPD 5 toward position D which is one end of the movable range in the direction of the body axis A of the patient M, and toward position E which is one end of the movable range in the transverse direction S. As shown in the lower left portion of FIG. 4, the X-ray grid 8 reaches position D which is one end of the movable range in the direction of the body axis A of the patient M. Then, as shown in the lower right portion of FIG. 4, the direction of movement in the direction of the body axis A of the patient M is reversed, and the X-ray grid 8 now starts moving toward position −D which is the other end. At this time, the relative movement of the X-ray grid 8 in the transverse direction S of the patient M remains toward position E. At the time of the state shown in the lower left portion of FIG. 4, the movement of the X-ray grid 8 in the transverse direction S of the patient M is not necessarily reversed toward position −E. That is, the movements of the X-ray grid 8 relative to the FPD 5 in the direction of the body axis A and the transverse direction S of the patient M are independent of each other. This arrangement renders the movement of the X-ray grid 8 relative to the FPD 5 further complicated.

The tomographic X-ray apparatus 30 according to Embodiment 2, as described above, can accommodate a reconstructing method in a tomographic X-ray apparatus using a well-known elongate X-ray beam. Therefore, embodiments of the tomographic X-ray apparatus can assume a wide variety, and this invention is adaptable to various applications.

This invention is not limited to the foregoing embodiments, but may be modified as follows:

(1) In each of the foregoing embodiments, the X-ray tube and FPD are synchronously moved along linear tracks. The X-ray tube and FPD may be modified to move along an arcuate track or helical tracks.

(2) The tomographic X-ray apparatus in each of the foregoing embodiments is a medical apparatus. This invention is also applicable to industrial and nuclear apparatus.

(3) The tomographic X-ray apparatus in each of the foregoing embodiments may be modified to carry out also spot radiography of a subject. That is, the X-ray grid according to this modification may be constructed to change the manner of movement relative to the FPD according to different radiographing modes.

(4) The movement of the X-ray grid relative to the FPD according to this invention is not limited to the manner described in each embodiment. For example, the X-ray grid may be moved relative to the FPD only along the body axis or only transversely of the subject. In this modification, it is more desirable to reverse the direction of relative movement during a serial acquisition of X-ray fluoroscopic images.

This invention may be embodied in other specific forms without departing from the spirit or essential attributes thereof and, accordingly, reference should be made to the appended claims, rather than to the foregoing specification, as indicating the scope of the invention.

What is claimed is:

1. A body section radiographic apparatus for serially acquiring a series of fluoroscopic images while synchronously moving a radiation source and a radiation detecting device in opposite directions to each other, and obtaining a sectional image of a subject from the series of fluoroscopic images, the apparatus comprising:
the radiation source for emitting a beam of radiation;
the radiation detecting device opposed to the radiation source and having a plurality of radiation detecting elements;
a synchronous moving device for moving the radiation source and the radiation detecting device synchronously with each other; and
a radiation grid disposed to cover a radiation detecting plane of the radiation detecting device for removing scattered radiation;
wherein the fluoroscopic images are serially acquired through moving the radiation grid relative to the radiation detecting device to move a position where the sectional image of the subject on a grid immobility section is protected on the radiation detecting device and a position where transmission unevenness of the radiation grid is projected on the radiation detecting device relative to the sectional image having the radiation grid being obtained by fixed support by the radiation detecting device,
the grid immobility section being a specific section where the radiation grid is immobile.

2. The body section radiographic apparatus according to claim 1, wherein the radiation grid is moved relative to the radiation detecting device, in a direction perpendicular to a synchronous moving direction of the radiation source and the radiation detecting device.

3. The body section radiographic apparatus according to claim 1, wherein the radiation grid is moved relative to the radiation detecting device, along a synchronous moving direction of the radiation source and the radiation detecting device.

4. The body section radiographic apparatus according to claim 2, wherein the radiation grid is moved relative to the radiation detecting device, along the synchronous moving, direction of the radiation source and the radiation detecting device.

5. The body section radiographic apparatus according to claim 1, wherein the radiation source and the radiation detecting device are synchronously movable along linear tracks.

6. The body section radiographic apparatus according to claim 2, wherein the radiation source and the radiation detecting device are synchronously movable along linear tracks.

7. The body section radiographic apparatus according to claim 3, wherein the radiation source and the radiation detecting device are synchronously movable along linear tracks.

8. The body section radiographic apparatus according to claim 4, wherein the radiation source and the radiation detecting device are synchronously movable along linear tracks.

9. A noise removing method for a body section radiographic apparatus for serially acquiring is series of fluoroscopic images while synchronously moving to radiation source and a radiation detecting device, and obtaining a sectional image of a subject from the series of fluoroscopic images, the method comprising:
moving the radiation source and the radiation detecting device synchronously with each other with a synchronous moving device, the radiation source emitting a beam of radiation and
the radiation detecting device being opposed to the radiation source and having a plurality of radiation detecting elements; and
covering a radiation detecting plane of the radiation detecting device with a radiation grid to remove scattered radiation; and
serially acquiring the fluoroscopic images while moving the radiation grid relative to the radiation detecting device to change positions where radiation transmission unevenness of the radiation grid is projected on the radiation detecting device.

10. The noise removing method according to claim 9, wherein the radiation grid is moved relative to the radiation detecting device, in a direction perpendicular to a synchronous moving direction of the radiation source and the radiation detecting device.

11. The noise removing method according to claim 9, wherein the radiation grid is moved relative to the radiation detecting device, along a synchronous moving direction of the radiation source and the radiation detecting device.

12. The noise removing method according to claim 10, wherein the radiation grid is moved relative to the radiation detecting device, along the synchronous moving direction of the radiation source and the radiation detecting device.

13. The noise removing method according to claim 11, wherein the radiation source and the radiation detecting device are synchronously moved along linear tracks.

14. The noise removing method according to claim 12, wherein the radiation source and the radiation detecting device are synchronously moved along linear tracks.

15. The noise removing method according to claim 13, wherein the radiation source and the radiation detecting device are synchronously moved along linear tracks.

16. The noise removing method according to claim 9, wherein the radiation source and the radiation detecting device are synchronously moved along an arcuate track.

17. The noise removing method according to claim 10, wherein the radiation source and the radiation detecting device are synchronously moved along an arcuate track.

18. The noise removing method according to claim 11, wherein the radiation source and the radiation detecting device are synchronously moved along an arcuate track.

* * * * *